United States Patent
Kariv et al.

(10) Patent No.: US 10,163,204 B2
(45) Date of Patent: Dec. 25, 2018

(54) TRACKING-BASED 3D MODEL ENHANCEMENT

(71) Applicant: St. Jude Medical International Holding S.à r.l., Luxembourg (LU)

(72) Inventors: Itay M. Kariv, Haifa (IL); Amit Cohen, Binyamina (IL); Uzi Eichler, Haifa (IL); Kobi Kor, Ramat Hsharon (IL)

(73) Assignee: St. Jude Medical International Holding S.à r.l., Luxembourg (LU)

( * ) Notice: Subject to any disclaimer, the term of this patent is extended or adjusted under 35 U.S.C. 154(b) by 119 days.

(21) Appl. No.: 15/042,613

(22) Filed: Feb. 12, 2016

(65) Prior Publication Data

US 2016/0239963 A1     Aug. 18, 2016

Related U.S. Application Data

(60) Provisional application No. 62/116,037, filed on Feb. 13, 2015.

(51) Int. Cl.
*G06K 9/00* (2006.01)
*G06T 7/00* (2017.01)
(Continued)

(52) U.S. Cl.
CPC ............ *G06T 7/0012* (2013.01); *A61B 5/042* (2013.01); *A61B 5/063* (2013.01); *A61B 6/12* (2013.01); *A61B 6/481* (2013.01); *A61B 6/5229* (2013.01); *G06T 7/11* (2017.01); *G06T 7/20* (2013.01); *G06T 7/70* (2017.01); *G06T 11/003* (2013.01);
(Continued)

(58) Field of Classification Search
CPC . G06T 7/0012; G06T 7/11; G06T 7/70; G06T 7/20; G06T 11/003; G06T 2207/30048; A61B 6/481; A61B 6/5229; A61B 6/12; A61B 6/4225; A61B 6/5264; A61B 6/4441; A61B 6/503; A61B 5/063; A61B 5/042; A61B 2576/023; A61B 2034/2051; A61B 34/20
USPC ....... 382/128, 154, 254, 115, 199, 131, 270; 128/920; 250/363.04; 378/4; 600/410,
(Continued)

(56) References Cited

U.S. PATENT DOCUMENTS

6,233,476 B1      5/2001   Strommer et al.
6,597,936 B1 *   7/2003   Liu ...................... G01R 33/563
                                                                       600/410
(Continued)

*Primary Examiner* — Aaron W Carter
(74) *Attorney, Agent, or Firm* — Dykema Gossett PLLC (57) ABSTRACT

A method for enhancing a three-dimensional (3D) reconstruction of an object comprises obtaining a signal indicative of a static 3D reconstruction of an object disposed in a tracking space, co-registering the 3D reconstruction to the 3D tracking space, collecting enhancement data from a tracked tool disposed in the 3D tracking space, and adding real-time features of the object to the static 3D reconstruction using the enhancement data. A system for enhancing data obtained by a medical system includes an electronic control unit configured to receive a first signal for a static 3D reconstruction of an organ, co-register the static 3D reconstruction to a 3D tracking space for a tracked tool, receive a second signal for enhancement data generated by the tracked tool operating within a region of interest of the organ, and add real-time features of the area of interest to the static 3D reconstruction using the enhancement data.

22 Claims, 5 Drawing Sheets

(51) Int. Cl.
   *A61B 6/12*      (2006.01)
   *A61B 6/00*      (2006.01)
   *A61B 5/042*     (2006.01)
   *A61B 5/06*      (2006.01)
   *G06T 7/20*      (2017.01)
   *G06T 11/00*     (2006.01)
   *G06T 7/70*      (2017.01)
   *G06T 7/11*      (2017.01)
   *A61B 34/20*     (2016.01)

(52) U.S. Cl.
   CPC .......... *A61B 6/4225* (2013.01); *A61B 6/4441* (2013.01); *A61B 6/503* (2013.01); *A61B 6/5264* (2013.01); *A61B 34/20* (2016.02); *A61B 2034/2051* (2016.02); *A61B 2576/023* (2013.01); *G06T 2207/30048* (2013.01)

(58) Field of Classification Search
   USPC ....... 600/420, 431, 499, 407, 437, 436, 645; 348/344, 355; 705/2, 3
   See application file for complete search history.

(56) References Cited

U.S. PATENT DOCUMENTS

| | | | | |
|---|---|---|---|---|
| 6,597,938 B2* | 7/2003 | Liu | ...................... | G01R 33/563 128/920 |
| 7,026,623 B2* | 4/2006 | Oaknin | ................ | A61B 6/4057 250/363.04 |
| 7,263,397 B2 | 8/2007 | Hauck et al. | | |
| 7,386,339 B2 | 6/2008 | Strommer et al. | | |
| 7,899,223 B2* | 3/2011 | Boese | .................. | A61B 5/0402 378/4 |
| 8,131,344 B2* | 3/2012 | Strommer | ............ | A61B 5/0555 600/411 |
| 8,195,292 B2 | 6/2012 | Rosenberg et al. | | |
| 8,199,244 B2* | 6/2012 | Baraniuk | ................ | H04L 25/20 348/335 |
| 8,238,625 B2 | 8/2012 | Strommer et al. | | |
| 8,295,577 B2* | 10/2012 | Zarkh | ..................... | A61B 6/12 382/132 |
| 8,463,363 B2* | 6/2013 | Blevis | .................... | A61B 6/037 382/199 |
| 8,623,369 B2* | 1/2014 | Abulrob | ........... | A61K 47/48561 424/130.1 |
| 9,351,782 B2* | 5/2016 | Stein | .................... | G06F 19/3406 |
| 2001/0031919 A1* | 10/2001 | Strommer | ............ | A61B 5/0066 600/424 |
| 2002/0049375 A1* | 4/2002 | Strommer | ............ | A61B 5/0066 600/407 |
| 2004/0097805 A1* | 5/2004 | Verard | ............... | A61B 1/00071 600/428 |
| 2005/0107688 A1* | 5/2005 | Strommer | ........... | A61B 5/0066 600/424 |
| 2006/0058647 A1* | 3/2006 | Strommer | ................ | A61B 5/06 600/434 |
| 2006/0064006 A1* | 3/2006 | Strommer | ................ | A61B 5/06 600/415 |
| 2006/0241445 A1* | 10/2006 | Altmann | .................. | A61B 8/12 600/443 |
| 2006/0253024 A1* | 11/2006 | Altmann | .................. | A61B 8/12 600/437 |
| 2006/0253029 A1* | 11/2006 | Altmann | .................. | A61B 5/06 600/466 |
| 2006/0253031 A1* | 11/2006 | Altmann | .................. | G06T 7/38 600/466 |
| 2006/0253032 A1* | 11/2006 | Altmann | ................ | A61B 5/042 600/466 |
| 2007/0060833 A1 | 3/2007 | Hauck | | |
| 2008/0091171 A1* | 4/2008 | Strommer | ................ | A61B 5/06 604/528 |
| 2008/0175463 A1* | 7/2008 | Strommer | ................ | G06K 9/32 382/131 |
| 2008/0183071 A1 | 7/2008 | Strommer et al. | | |
| 2008/0287803 A1* | 11/2008 | Li | ........................... | A61B 8/12 600/466 |
| 2009/0182224 A1 | 7/2009 | Shmarak et al. | | |
| 2009/0216114 A1 | 8/2009 | Gorges et al. | | |
| 2011/0021903 A1* | 1/2011 | Strommer | .............. | A61B 5/042 600/410 |
| 2011/0054308 A1 | 3/2011 | Cohen et al. | | |
| 2011/0160569 A1* | 6/2011 | Cohen | ..................... | A61B 5/06 600/424 |
| 2011/0160571 A1* | 6/2011 | Cohen | ..................... | A61B 5/06 600/424 |
| 2011/0230758 A1* | 9/2011 | Eichler | ..................... | A61B 5/06 600/424 |
| 2011/0237933 A1* | 9/2011 | Cohen | ..................... | A61B 5/062 600/424 |
| 2012/0071753 A1* | 3/2012 | Hunter | ................. | A61B 1/2676 600/424 |
| 2012/0265054 A1 | 10/2012 | Olson | | |
| 2013/0172730 A1 | 7/2013 | Cohen | | |
| 2013/0184569 A1* | 7/2013 | Strommer | ............. | G16H 50/50 600/424 |
| 2013/0324833 A1 | 12/2013 | Barley et al. | | |
| 2015/0283319 A1* | 10/2015 | Tolkowsky | .............. | A61B 6/12 600/431 |
| 2016/0203608 A1* | 7/2016 | Izmirli | ................ | A61B 5/0402 382/128 |
| 2016/0239963 A1* | 8/2016 | Kariv | .................... | G06T 7/0012 |
| 2017/0086759 A1* | 3/2017 | Eichler | ................... | A61B 6/12 |
| 2017/0151023 A1* | 6/2017 | Shmarak | ................ | A61B 34/20 |
| 2017/0270661 A1* | 9/2017 | Strommer | ................ | G06K 9/32 |

\* cited by examiner

TRACKING-BASED 3D MODEL ENHANCEMENT

CROSS-REFERENCE TO RELATED APPLICATIONS

This application claims the benefit of U.S. provisional application No. 62/116,037, filed 13 Feb. 2015, which is hereby incorporated by reference as though fully set forth herein.

BACKGROUND a. Field of the Disclosure

The present disclosure relates generally to medical imaging and positioning systems that generate three-dimensional (3D) reconstructions of internal organs. In particular, the present disclosure relates to adding functional enhancements to 3D reconstructed models.

b. Background Art

Various methods exist for generating three-dimensional (3D) reconstructions of internal organs. For example, Computer Tomography (CT), X-ray, Positron Emission Tomography (PET) or Magnetic Resonance Imaging (MRI) may be used to generate a 3D modality that can be projected over fluoroscopy or some other two-dimensional (2D) image. Superimposing a real-time representation of an interventional medical device, such as a catheter or a guide wire, tracked by a Medical Positioning System (MPS), on the 3D reconstruction during a medical procedure is also known in the art.

The 3D reconstruction serves as a map to aid medical staff performing a medical procedure in navigating the medical device within a volume of interest in a body of a patient subjected to the procedure. In order for the superposition to reflect the true position of the medical device within the volume of interest, it is required to register the coordinate system associated with the MPS with the coordinate system associated with the 3D reconstruction.

Furthermore, it is desirable for medical professionals to view the medical device in real-time within the 3D reconstruction while maneuvering medical devices and performing therapy within the patient. Oftentimes, though, it is undesirable or even impossible to capture an image of the anatomy while maneuvering medical devices within the patient. For example, operating constraints associated with some body organs and blood vessels can prevent the simultaneous capture of images showing medical devices and images of the anatomy, particularly where a contrast agent or special dye is utilized.

To illustrate, medical imaging systems may be used to assist with cardiac resynchronization therapy (CRT) implantation procedures. In such procedures, a lead for a medical device is advanced through a coronary sinus ostium of a patient, where the ostium is the orifice of the coronary sinus, to deliver therapy. One way to obtain a representation of the coronary sinus is to take a venogram of the anatomy with a fluoroscopic imaging system. Contrast agent may be injected within the coronary sinus or other organ or blood vessels to facilitate the acquisition of the venogram with the imaging system. The contrast agent may even be trapped within the coronary sinus by positioning a balloon catheter within the coronary sinus ostium. The contrast agent highlights the anatomical structure of the coronary sinus on the venogram. Yet the balloon catheter must be removed before the medical devices, such as guide wires, catheters, and the LV lead, are advanced through the coronary sinus ostium. Thereafter, the contrast agent may disperse from the coronary sinus. Thus, the beneficial effect of the contrast agent highlighting the anatomical structure can be lost before the medical devices are navigated through the patient to the target location. The medical professional must then navigate the medical devices through the patient while only receiving partially highlighted images of the coronary sinus.

Though prior art 3D reconstructions have been able to combine images, models and information from many different sources, such as using CT or MRI projected over fluoroscopy, including historical information from tracked tools, such as Ensite™ NavX™ or MediGuide™ gMPS™ (guided Medical Positioning System) enabled devices (both of which are commercially available from St. Jude Medical, Inc.), such 3D reconstructions rely on stored image data. Thus, the 3D reconstructions do not reflect current, real-time conditions of tissue, as can be influenced by respiration of the patient and activation of the heart.

BRIEF SUMMARY

In one embodiment, a method for enhancing a three-dimensional (3D) reconstruction of an internal organ of a patient disposed in a tracking space comprises obtaining a signal indicative of a static 3D reconstruction of an object disposed in a tracking space, co-registering the 3D reconstruction to the 3D tracking space, collecting enhancement data from a tracked tool disposed in the 3D tracking space, and adding real-time features of the object to the static 3D reconstruction using the enhancement data.

In another embodiment, a system for enhancing data acquired from a medical system comprises an electronic control unit (ECU) configured to receive a first signal for a static 3D reconstruction of an organ, co-register the static 3D reconstruction to a 3D tracking space for a tracked tool, receive a second signal for enhancement data generated by the tracked tool operating within a region of interest of the organ, and add real-time features of the area of interest to the static 3D reconstruction using the enhancement data.

DETAILED DESCRIPTION

The present disclosure allows for a 3D reconstructed model to be enhanced with supplemental data during real-time manipulation of tools by the operator, regardless of how the 3D reconstructed model was originally created. By this approach, features that originally did not exist in the model (motion, missing or partial branches, etc.) become available for the benefit of the operator.

Figure 1:
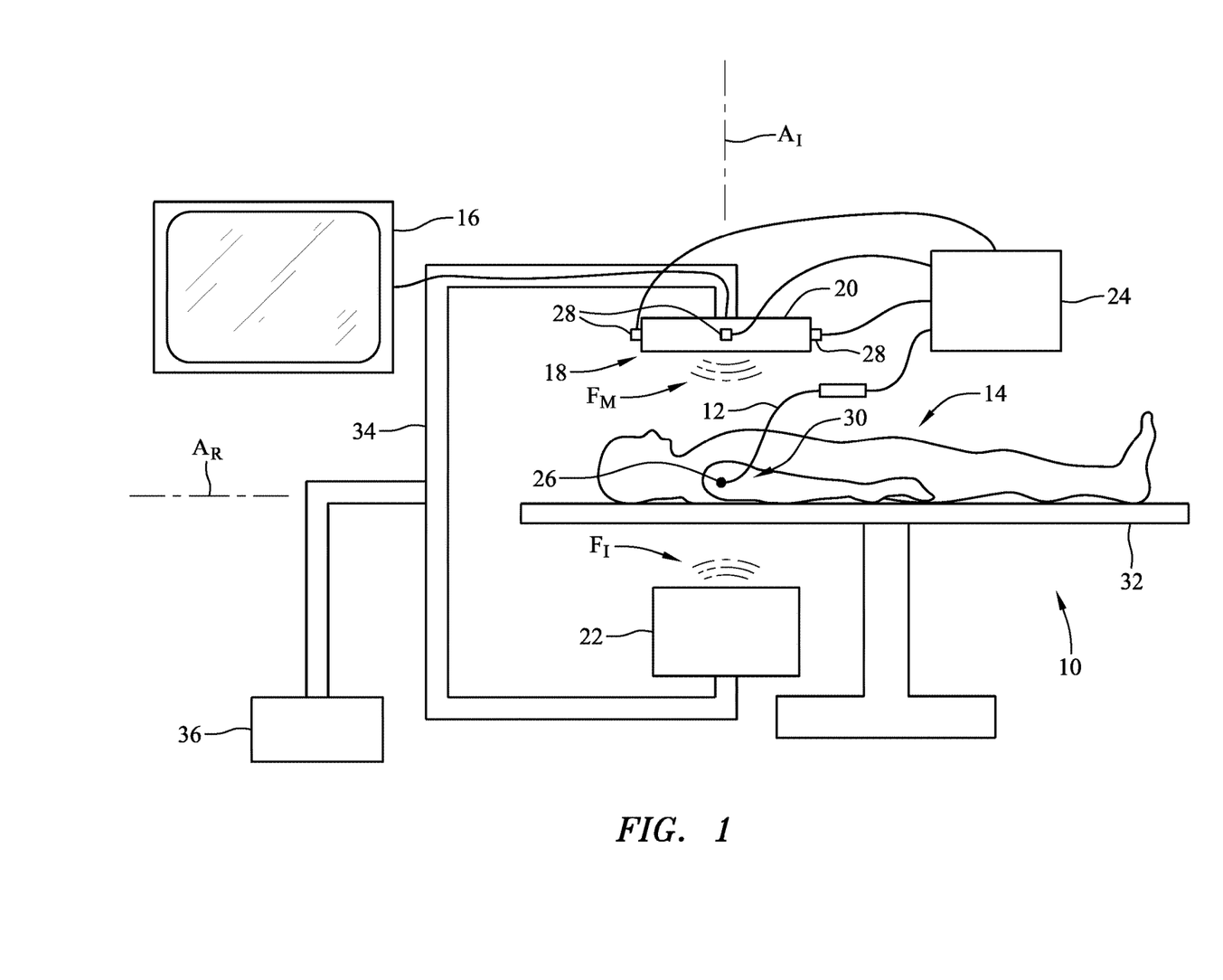
FIG. 1 is a schematic illustration of a medical imaging system for generating and displaying enhanced 3D reconstructions on a display screen.

FIG. 1 is a schematic illustration of medical imaging system 10 for determining the position of catheter 12 relative to a 3D reconstructed model of an organ of patient 14, as well as for generating and displaying tracking-based enhancement information on display unit 16. System 10 includes moving imager 18, which includes intensifier 20 and emitter 22, and medical positioning system 24, which includes positioning sensor 26 and field generators 28. Electrophysiology map information and cardiac mechanical activation data pertaining to the model generated by medical imaging system 10 are displayed on computer display 16 to facilitate treatment and diagnosis of patient 14. The present disclosure describes a way for system 10 to gather physiological information from patient 14 in order to enhance the 3D reconstructed model in order to facilitate diagnosis and treatment. For example, system 10 can be configured to collect cardiac motion and respiration motion data with catheter 12, and to further merge that data with the 3D model in a visual format. In another embodiment, the 3D reconstructed model is enhanced with anatomical features obtained by catheter 12 that were lacking in the originally obtained 3D reconstructed model.

Moving imager 18 is a device that acquires an image of region of interest 30 while patient 14 lies on operation table 32. Intensifier 20 and emitter 22 are mounted on C-arm 34, which is positioned using moving mechanism 36. In one embodiment, moving imager 18 comprises a fluoroscopic or X-ray type imaging system that generates a two-dimensional (2D) image of the heart of patient 14.

Medical positioning system (MPS) 24 includes a plurality of magnetic field generators 28 and catheter 12, to which positioning sensor 26 is mounted near a distal end. MPS 24 determines the position of the distal portion of catheter 12 in a magnetic coordinate system generated by field generators 28, according to output of positioning sensor 26. In one embodiment, MPS 24 comprises a Mediguide™ gMPS™ magnetically guided medical positioning system, as is commercially offered by St. Jude Medical, Inc., that generates a three-dimensional (3D) model of the heart of patient 14. In other embodiments, MPS 24 may comprise an impedance-based system such as, for example, an EnSite™ Velocity™ system utilizing EnSite™ NavX™ technology commercially available from St. Jude Medical, Inc., or as seen generally, for example, by reference to U.S. Pat. No. 7,263,397, or U.S. Pub. No. 2007/0060833, both of which are hereby incorporated by reference in their entireties as though fully set forth herein. Furthermore, hybrid magnetic and impedance based systems may be used.

C-arm 34 is oriented so that intensifier 20 is positioned above patient 14 and emitter 22 is positioned underneath operation table 32. Emitter 22 generates, and intensifier 20 receives, imaging field $F_I$, e.g., a radiation field, that generates a 2D image of area of interest 30 on display 16. Intensifier 20 and emitter 22 of moving imager 18 are connected by C-arm 34 so as to be disposed at opposites sides of patient 14 along imaging axis $A_I$, which extends vertically with reference to FIG. 1 in the described embodiment. Moving mechanism 36 rotates C-arm 34 about rotational axis $A_R$, which extends horizontally with reference to FIG. 1 in the described embodiment. Moving mechanism 36 or an additional moving mechanism may be used to move C-arm 34 into other orientations. For example, C-arm 34 can be rotated about an axis (not shown) extending into the plane of FIG. 1 such that imaging axis $A_I$ is rotatable in the plane of FIG. 1. As such, moving imager 18 is associated with a 3D optical coordinate system having x-axis $X_I$, y-axis $Y_I$, and z-axis $Z_I$.

Medical positioning system (MPS) 24 is positioned to allow catheter 12 and field generators 28 to interact with system 10 through the use of appropriate wiring or wireless technology. Catheter 12 is inserted into the vasculature of patient 14 such that positioning sensor 26 is located at area of interest 30. In the described embodiment, field generators 28 are mounted to intensifier 20 so as to be capable of generating magnetic field $F_M$ in area of interest 30 coextensive with imaging field $F_I$. In other embodiments, field generators 28 may be mounted elsewhere, such as under operation table 32. MPS 24 is able to detect the presence of position sensor 26 within magnetic field $F_M$. In one embodiment, position sensor 26 may include three mutually orthogonal coils, as described in U.S. Pat. No. 6,233,476 to Strommer et al., which is hereby incorporated by reference in its entirety for all purposes. As such, MPS 24 is associated with a 3D magnetic coordinate system having x-axis $X_P$, y-axis $Y_P$, and z-axis $Z_P$.

The 3D optical coordinate system and the 3D magnetic coordinate system are independent of each other, that is they have different scales, origins and orientations. Movement of C-arm 34 via moving mechanism 36 allows imaging field $F_I$ and magnetic field $F_M$ to move relative to area of interest 30 within their respective coordinate system. However, field generators 28 are located on intensifier 20 so as to register the coordinate systems associated with moving imager 18 and MPS 24. In embodiments where field generators 28 are not mounted on intensifier 20, registration between magnetic field $F_M$ and imaging field $F_I$ is maintained using other known methods. Thus, images generated within each coordinate system can be merged into single image shown on display unit 16. Moving imager 18 and MPS 24 may function together as is described in Publication No. US 2008/0183071 to Strommer et al., which is hereby incorporated by reference in its entirety for all purposes.

Display unit 16 is coupled with intensifier 20. Emitter 22 transmits radiation that passes through patient 14. The radiation is detected by intensifier 20 as a representation of the anatomy of area of interest 30. An image representing area of interest 30 is generated on display unit 16, including an image of catheter 12. C-arm 34 can be moved to obtain multiple 2D images of area of interest 30, each of which can be shown as a 2D image on display unit 16.

Display unit 16 is coupled to MPS 24. Field generators 28 transmit magnetic fields that are mutually orthogonal, corresponding to axes of the 3D magnetic coordinate system. Position sensor 26 detects the magnetic fields generated by field generators 28. The detected signals are related to the position and orientation of the distal end of catheter 12 by, for example, the Biot Savart law, known in the art. Thus, the precise position and location of the distal end of catheter 12 is obtained by MPS 24 and can be shown in conjunction with the 2D images of area of interest 30 at display unit 16. Furthermore, data from position sensor 26 can be used to generate a 3D model of area of interest 30, as is described in U.S. Pat. No. 7,386,339 to Strommer et al., which is hereby incorporated by reference in its entirety for all purposes.

In one embodiment, system 10 is integrated with an impedance-based mapping and navigation system, including, for example, an EnSite™ NavX™ system commercially available from St. Jude Medical, Inc., or as seen generally, for example, by reference to U.S. Pat. No. 7,263,397, or Pub. No. US 2007/0060833, both of which are hereby incorporated by reference in their entireties for all purposes. Information from such impedance-based systems can be co-registered and combined with data from MPS 24 of FIG. 1. MPS 24 and the impedance-based system can be structurally integrated, such as is described in Pub. No. US 20012/0265054 to Olson, which is hereby incorporated by reference in its entireties for all purposes.

3D models and data generated by system 10 can be used to facilitate various medical procedures. For example, it has been found that mechanical activation data, e.g., displacement of heart wall muscle, may be used in conjunction with electrical mapping data to optimize the placement of leads for cardiac resynchronization therapy (CRT) procedures. U.S. Pat. No. 8,195,292 to Rosenberg et al., which is hereby incorporated by reference in its entirety for all purposes, describes exemplary methods for optimizing CRT using electrode motion tracking.

In typical imaging systems, observing, understanding and assessing real-time data from the anatomy can be difficult when the 3D model is static and not reflecting real-time motion of the anatomy. 3D models generated by these typical systems require the operator or physician to mentally reconcile real-time motion with a static 3D model. Thus, diagnosis and treatment of the patient can be encumbered by the skill of the physician.

The present disclosure provides system 10 with the capability of obtaining and displaying a 3D model along with real-time data points collected during a medical procedure utilizing a catheter or some other tracking device. In particular, the real-time data points can be added to the static 3D model as heart wall motion imaging (e.g., displacement and timing), respiration movement, and extended anatomical features. Real-time features from the data points include real-time position data and real-time physiological data, as described throughout the application. The systems and methods of the present technique allow system 10 to overcome the disadvantages of the prior art by providing a method and a system for registering a coordinate system associated with a three dimensional (3D) pre-acquired medical image ("a 3D coordinate system") with a 3D coordinate system associated with an MPS ("MPS coordinate system") and with a 2D coordinate system associated with a 2D image ("2D coordinate system"), compensating the 3D pre-acquired medical image and the 2D image for respiration and cardiac motion, enhancing the registered images with real-time tracking data to generate supplemental anatomical information, and simultaneously displaying all images, models and data in real-time alone or in combination with each other. It is noted that the MPS coordinate system is a 3D coordinate system.

System 10, according to the disclosed technique, pre-acquires a 3D image (FIG. 2A) of a volume of interest, and extracts a 3D image model (FIG. 2B) from the 3D image of at least one tubular organ (e.g., the coronary vessel of the heart) within a volume of interest. System 10 further obtains an estimated volumetric model (FIG. 3C) of the same tubular organ. System 10 obtains this estimated volumetric model using a trace (FIG. 3A) of a medical device (i.e., a set of locations representing the trajectory of the medical device), which is inserted into the tubular organ, and at least one 2D image (FIG. 3B) of that same organ. The medical device is fitted with an MPS sensor in order to generate the trace. System 10 uses these models and the above-mentioned coordinate systems to achieve registered images and models with higher degrees of accuracy (FIG. 4). Such registration procedures are described in U.S. Pat. No. 8,238,625 to Strommer et al., which is hereby incorporated by reference in its entirety for all purposes. The term "registration" refers to finding a transformation associating the coordinates of each point in one coordinate system to the coordinates of the same point in another coordinate system.

Additionally, system 10, according to the disclosed technique, compensates the registered coordinate systems for both cardiac and respiratory motion, as is described in Pub. No. US 2013/0172730 to Cohen, which is hereby incorporated by reference in its entirety for all purposes.

Figures 3A, 3B, 3C:
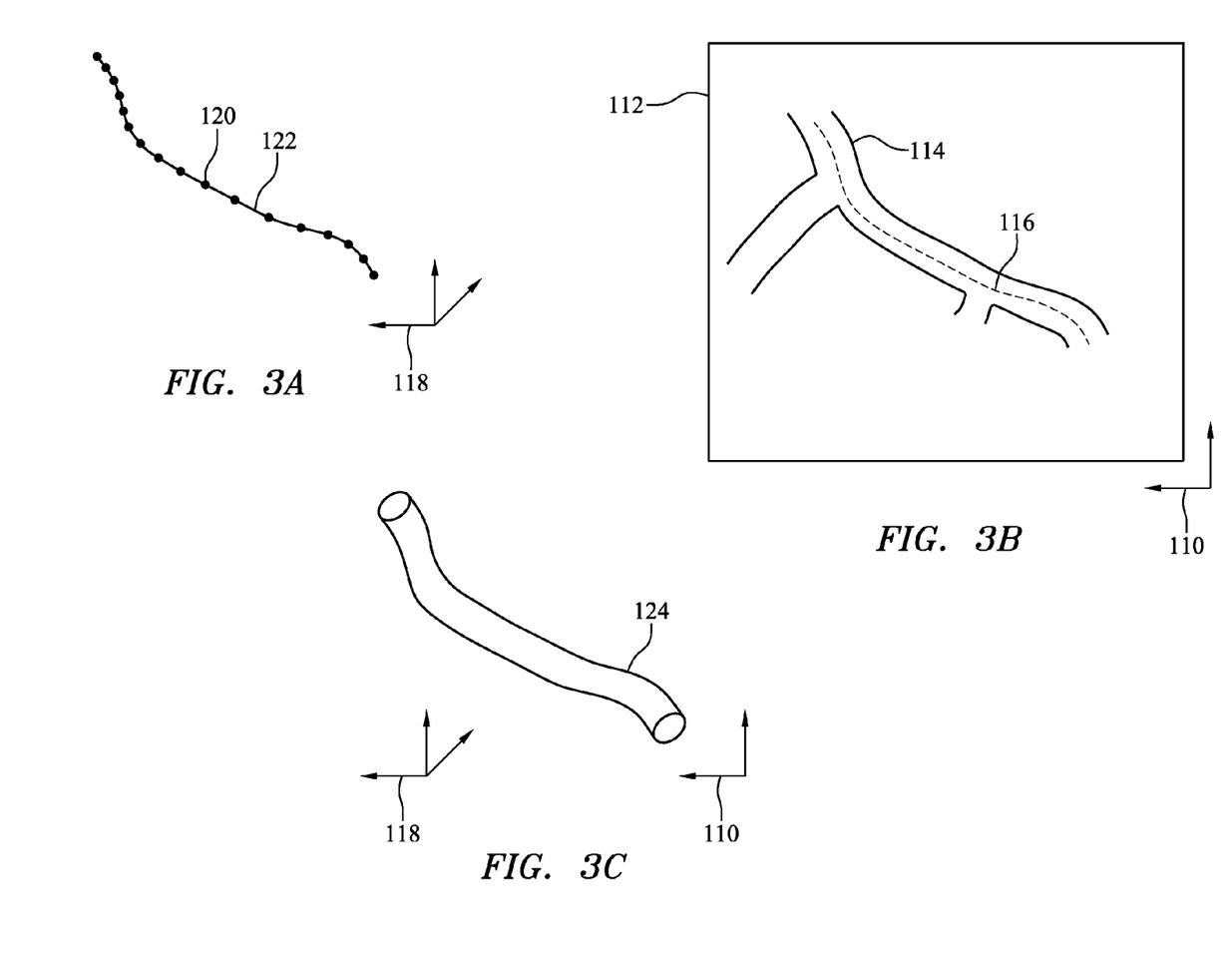
FIG. 3A is a schematic illustration of a trace of a medical device, such those used in FIG. 1, in accordance with the disclosed technique.
FIG. 3B is a schematic illustration of a 2D image of a volume of interest including a 2D representation of the tubular organ of FIG. 2B.
FIG. 3C is a schematic illustration of an estimated volumetric model of the tubular organ determined from the medical device trace of FIG. 3A and the 2D representation of FIG. 3B.
Figure 4:
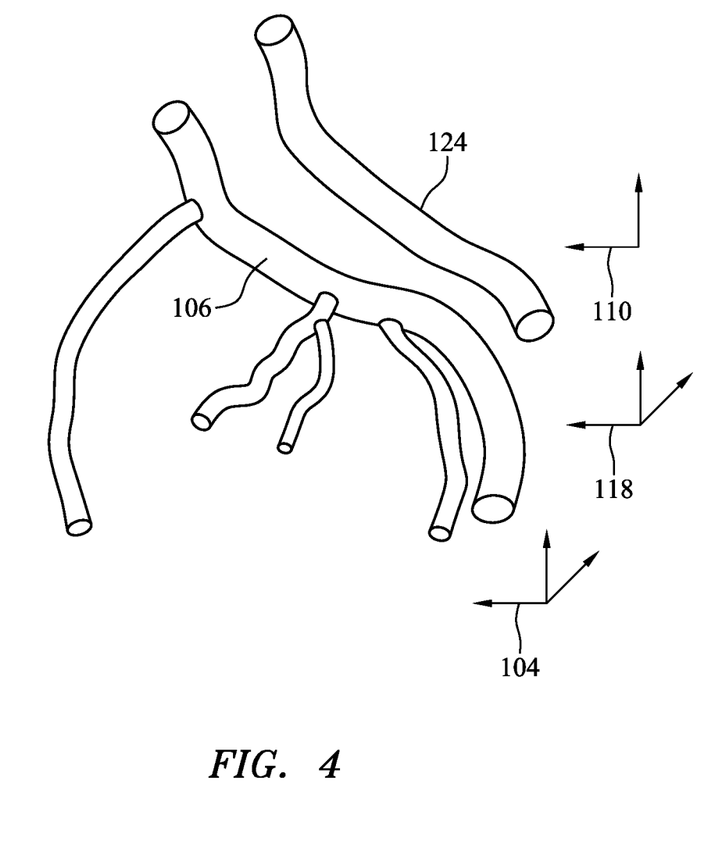
FIG. 4 is a schematic illustration of the estimated volumetric model of FIG. 3C being registered with the extracted 3D model of FIG. 2B according to the process of the disclosed technique.

Furthermore, with the techniques described herein, system 10 is able to utilize real-time information obtained with a tracking tool, such as that used to generate the trace of FIG. 3A, to enhance the registered images (FIG. 5), whether displayed together or individually, such as the 2D image of FIG. 3B or the estimated volumetric model of FIG. 3C.

Figure 2A:
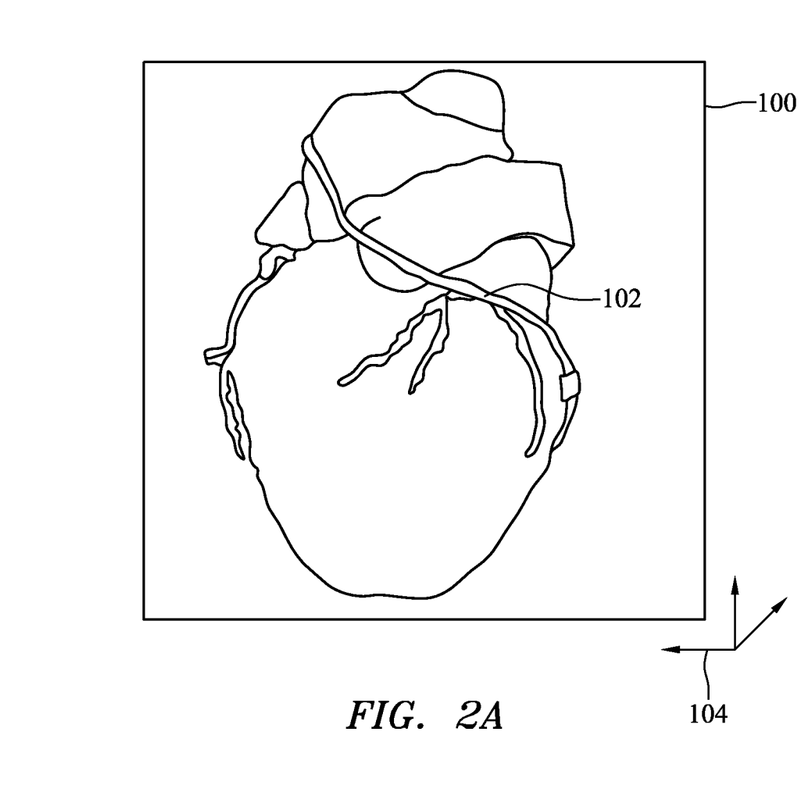
FIG. 2A is a schematic illustration of a 3D pre-acquired image associated with a 3D coordinate system in accordance with the disclosed technique.

FIG. 2A is a schematic illustration of 3D pre-acquired image 100 associated with 3D coordinate system 104 in accordance with the disclosed technique. 3D pre-acquired image 100 may be acquired using any suitable system, e.g., CT, Mill, PET, 3D Ultra Sound, etc. Image 100 is a 3D image of a volume of interest which includes tubular organ 102. 3D pre-acquired image 100 serves as a 3D reference road-map for navigating a minimally invasive medical device, such as catheter 12 of FIG. 1, in the volume of interest. Superimposing a minimally invasive medical device, operative in an MPS coordinate system and fitted with an MPS sensor, on 3D pre-acquired image 100, requires registering the 3D coordinate system with the MPS coordinate system.

Figure 2B:
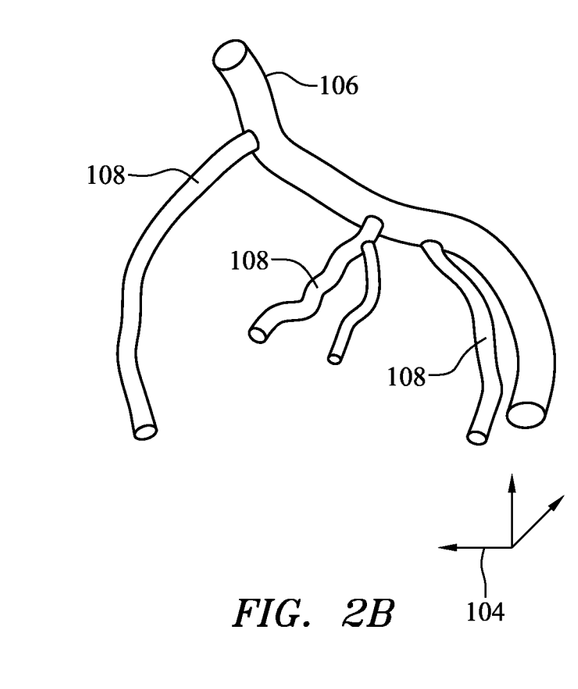
FIG. 2B is a schematic illustration of a 3D image model of a tubular organ extracted from the 3D pre-acquired image of FIG. 2A.

FIG. 2B is a schematic illustration of 3D image model 106, of tubular organ 102, extracted from 3D pre-acquired image 100 (FIG. 2A). In one embodiment, the tubular organ comprises a coronary sinus having branches 108. Extracted image model 106 is also associated with 3D coordinate system 104. To achieve the registration, prior to a medical procedure, system 10, according to the disclosed technique, processes (e.g., segments) 3D pre-acquired image 100 and extracts 3D model 106 of tubular organ 102. Tubular organ 102 is situated within the imaged volume of interest.

FIG. 3A is a schematic illustration of trace 122 of a medical device (e.g. catheter 12 of FIG. 1) in accordance with the disclosed technique. Trace 122 is constructed from a plurality of MPS points, such as MPS point 120, representing the locations of the MPS sensor (e.g. sensor 26 of FIG. 1), fitted on the medical device. During a medical procedure (e.g., minimally invasive procedure), the medical staff inserts a catheter fitted with an MPS sensor (e.g. catheter 12 of FIG. 1), into tubular organ 102 and moves the catheter along (i.e., pushed forward or pulls back within) tubular organ 102 to acquire points 120. An MPS (e.g. medical positioning system 24 of FIG. 1) acquires a plurality of MPS points (i.e., a plurality of locations of the MPS sensor within and along the tubular organ), and determines 3D MPS trace 122 of the shape of tubular organ 102. These MPS points are represented by coordinates in MPS coordinate system 118. The terms "trace" and "centerline" both refer herein to a set of locations representing the trajectory of the medical device.

FIG. 3B is a schematic illustration of 2D image 112 of the volume of interest. 2D image 112 includes 2D representation 114 of tubular organ 102, and trajectory 116 of the medical device inside tubular organ 102. 2D image 112 is associated with 2D coordinate system 110. When the medical staff inserts the medical device fitted with an MPS sensor into tubular organ 102, system 10 separately obtains a 2D real-time image of that organ, thereby capturing both representation 114 and trajectory 116 together. 2D image 112 may be obtained using any suitable methods, such as X-ray, 2D Ultra Sound, etc. When system 10 according to the disclosed technique, uses an X-ray imager to generate a venogram, such as moving imager 18 of FIG. 1, to obtain 2D image 112, it is desirable to inject the tubular organ with a contrast fluid (e.g. a dye) to increase apparentness of 2D representation 114 of the tubular organ in image 112.

Since MPS coordinate system 118 is registered with 2D coordinate system 110, each of the MPS points, such as MPS point 120, has a corresponding point in 2D coordinate system 110. Using image processing techniques, such as segmentation or edge detection, system 10 determines the width of 2D representation 114 of tubular organ 102 for each MPS point. System 10 uses this width, together with trace 122 of the medical device (i.e., not necessarily the centerline of tubular organ 102), to determine an estimated volumetric model of tubular organ 102. For example, the width of 2D representation 114 of tubular organ 102, at each MPS point, determines the diameter of a circle encircling that point.

FIG. 3C is a schematic illustration of estimated volumetric model 124 of tubular organ 102 determined from trace 122 (FIG. 3A) and 2D representation 114 (FIG. 3B). Estimated volumetric model 124 is associated with MPS coordinate system 118 and with 2D coordinate system 110. MPS coordinate system 118 is registered with 2D coordinate system 110 (e.g., by mechanically coupling MPS transmitters/field generators 28 to moving imager 18, as described above with reference to FIG. 1). Using 3D MPS trace 122 and at least one 2D image, system 10 estimates volumetric model 124 of tubular organ 102. In one embodiment, volumetric model 124 comprises an Angio Survey™ 3D model generated using MediGuide™ Technology. Angio Survey™ features a capability to reconstruct a 3D model of a vascular anatomical structure from two cine-loops where contrast agent is used, recorded at different projections. The reconstructed model can be displayed in 3D and projected on live and pre-recorded fluoroscopy. In one embodiment, a MediGuide™ CPS Courier 0.014 inch (~0.3556 mm) guide wire is used with the Angio Survey model.

System 10 registers estimated volumetric model 124, MPS coordinate system 118 and 3D coordinate system 104 by matching extracted image model 106 with estimated volumetric model 124. System 10 achieves this registration with a high degree of accuracy, (i.e., since a volumetric model represents the tubular organ with a higher degree of accuracy than a simple trace of the trajectory of the MPS sensor within the tubular organ). Since 2D coordinate system 110 is registered with MPS coordinate system 118, and MPS coordinate system 118 is registered with 3D coordinate system 104, 2D coordinate system 110 is also registered with 3D coordinate system 104.

FIG. 4 is a schematic illustration of a registration process in accordance with the disclosed technique. System 10 registers MPS coordinate system 118 with 3D coordinate system 104, for example, by matching extracted 3D model 106 with estimated volumetric model 124. Consequent to this registration, 2D coordinate system 110 is also registered with coordinate system 104. Thus, each point, in each one of coordinate systems 110, 118 and 104, has a corresponding point in each of the other coordinate systems. This registration, between coordinate systems 110, 118 and 104, enables superimposing MPS points of interest, at their respective locations on a 3D image. For example, 3D pre-acquired image 100 may now serve, for example, as a roadmap for the medical staff, during medical procedures (e.g., treating structural heart disease, deployment of percutaneous valves, ablation, mapping, drug delivery, ICD/CRT lead placement, deploying a stent and other PCI procedures, surgery, biopsy). On this 3D reference roadmap, system 10 superimposes 3D trace 122 of the medical device within tubular organ 102. This registration further enables superimposing points of interest included in 3D image 100, at their respective location on 2D image 112. As a further example, 3D image model 106 of tubular organ 102 may be projected onto 2D image 112. Thus, the projected 3D image may serve as a virtual dye, instead of injecting a fluoroscopic dye to tubular organ 102 prior to obtaining 2D image 112.

During the medical procedure, the position and orientation of patient 14 might change. Consequently, the 2D real-time representation of the volume of interest may also change. These changes may affect the registration between 3D coordinate system 104 and 2D coordinate system 110. Therefore, an MPS reference sensor, placed on patient 14 during the medical procedure, is operative to detect these changes in the patient position and orientation. The information about these changes may be used either for triggering a registration process or as input for such a registration process. All of the registration processes described herein are explained in greater detail in the aforementioned '625 patent to Strommer et al.

Additionally, after registration of the images, movement of each image due to biomechanical effects, such as respiration of the patient and beating of the heart, is compensated for using techniques of the aforementioned Pub. No. US 2013/0172730 to Cohen, which are summarized below. For example, one technique for motion compensation comprises using physical anchors, which may comprise MPS sensors, that serve as common position and orientation markers by which system 10 associates data from the different coordinate systems. Likewise, virtual anchors may be used to perform motion compensation, as is described in Pub. No. US 2011/0054308 to Cohen et al., which is hereby incorporated by reference in its entirety for all purposes. Additionally, an internal position reference sensor can be used to generate a motion compensation function based on a vector of the internal position reference sensor as the patient moves, as is described in Pub. No. US 2011/0158488 to Cohen et al., which is hereby incorporated by reference in its entirety for all purposes. As another example, one technique for motion compensation comprises continuously monitoring the positions of MPS sensors as they are positioned with a patient's body during first and second time period frequencies, whereby system 10 can learn the frequencies of specific points of the anatomy so that the location of those points within the various coordinate systems at the moment an image or model is acquired allows system 10 to determine the cardiac and respiratory phases of the patient's body, as is described in Pub. No. US 2009/0182224 to Shmarak et al., which is hereby incorporated by reference in its entirety for all purposes.

Finally, with respect to the present disclosure, the registered, compensated models and/or images can be enhanced with real-time tracking data, which can be extrapolated to extend the boundary of the previously generated 3D reconstructed model, or generate tissue motion visualization on the previously generated 3D reconstructed model, as is discussed with reference to FIG. 5.

Figure 5:
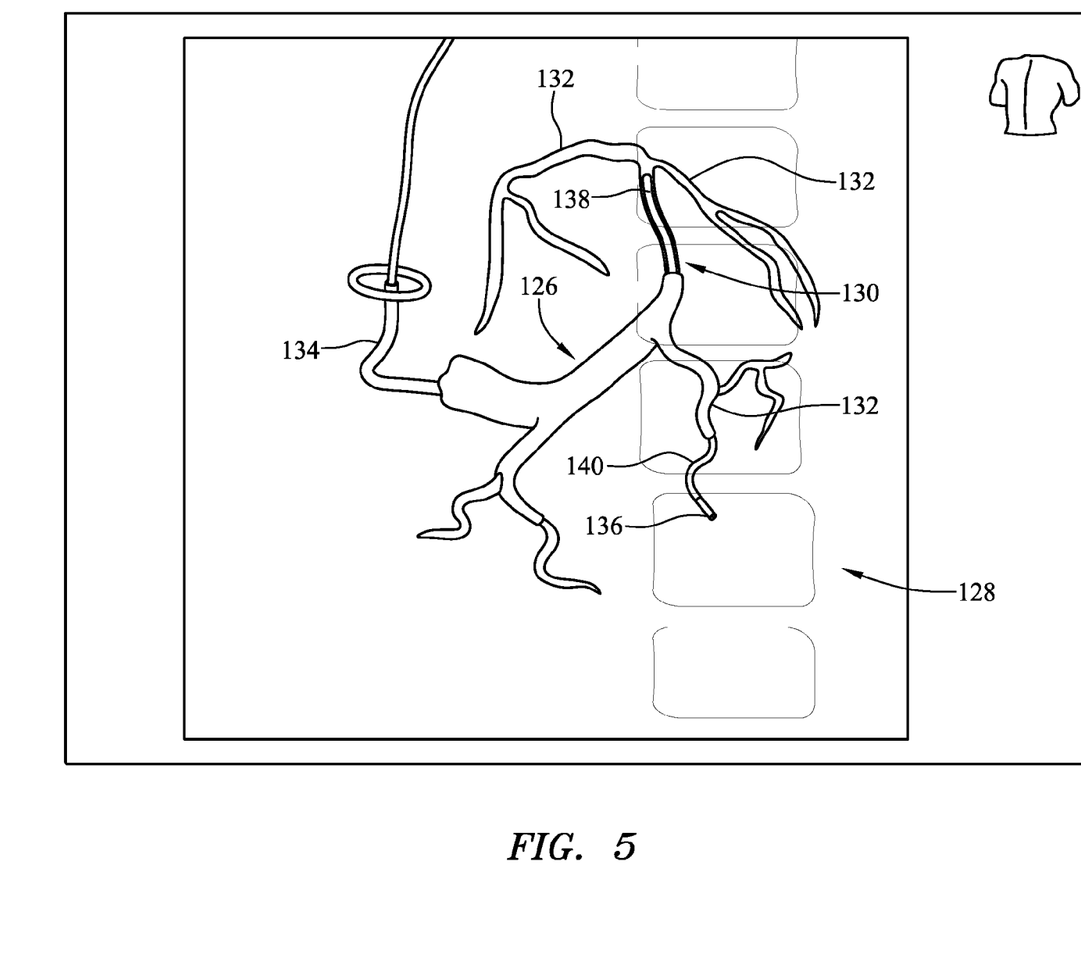
FIG. 5 is a schematic illustration of a 3D reconstructed model, such as that of FIG. 2B, superimposed over a 2D image, such as that of FIG. 3B, along with real-time, tracking-based enhancements according to the disclosed technique.

FIG. 5 is a schematic illustration of 3D reconstructed model 126 superimposed over 2D image 128 along with real-time, tracking-based enhancements of the present technique. 2D image 128 additionally includes contrast fluid-enhanced portions of anatomy such that coronary sinus 130 and branches 132 are distinctly visible. Catheter 134 is shown inserted into coronary sinus 130 such that tip 136 extends from one of branches 132. In the described embodiment, the real-time, tracking-based enhancements comprise trace 138 and trace 140.

In one embodiment, 2D image 128 is generated using X-ray, such as described with reference to FIG. 3B. In one embodiment, 3D reconstructed model 126 is generated using tracking information generated by tip 136 of catheter 134, which may comprise a MediGuide-enabled tip as described above with reference to FIG. 1. In another embodiment, 3D reconstructed model 126 may be generated using an estimated volumetric model as discussed with reference to FIG. 3C. In other embodiments, 3D reconstructed model 126 may be generated using a combination of imaging (angiography, CT, MRI, ultrasound, etc.) and 3D tracking data.

As catheter 134 is traversed through coronary sinus 130, tip 136 generates real-time position data and real-time physiological data. The position data is influenced by its location within the anatomy. Thus, as tip 136 moves along each branch 132, the position of each branch 132 is traced as the tissue guides tip 136 within the various coordinate systems. However, the location of each branch 132 within the coordinate system does not remain stationary as patient 14 breaths and the heart of patient 14 beats. Furthermore, the contrast fluid used to show coronary sinus 130 dissipates over time, making the visibility of branches 132 difficult to perceive, or the contrast fluid may not extend all the way to the end of each branch 132. As such, it can be difficult to know the actual location of catheter 134 and tip 136 relative to coronary sinus 130 and branches 132.

The techniques of the present disclosure enhance 3D reconstructed model 126 of coronary sinus 130 by means of collecting 3D tracking data of tip 136 while it is manipulated within the volume of that organ. As described above, 3D reconstructed model 126 is co-registered to the 3D tracking space. Specifically, the coordinate system of 3D reconstructed model 126 is co-registered with the coordinate system of catheter 134, e.g., 3D coordinate system 104 is co-registered with MPS coordinate system 118. As such, the tracking data can be associated with any of 3D reconstructed model 126, 2D image 128, 3D image model 106, estimated volumetric model 124 and 2D image 112. The tracking data may include location data, e.g., coordinates in each of the coordinate systems, as well as physiological data (e.g., cardiovascular data and/or electrical data, such as impedance, resistance, conductivity, etc.).

In one embodiment, catheter 134 collects enhancement data that is used to extend existing portions of 3D reconstructed model 126 beyond its boundaries as originally reconstructed. For example, 3D reconstructed model 126, which may be generated using multiple angiograms, may not fully represent coronary sinus 130, such as by not fully extending throughout branches 132. In particular, contrast fluid used with 2D image 128 may have low penetration into some areas of branches 132, thus making it difficult to generate 3D reconstructed model 126. Thus, once a tracked tool, such as catheter 134, is manipulated through one of branches 132 beyond an edge of 3D reconstructed model 126, a skeleton of the extending anatomy can be reconstructed based on trace 140 from tip 136. As such, the shape of 3D reconstructed model 126 is extended beyond its original borders and the model is further built-out. This enables the operator of system 10 to better comprehend the orientation of catheter 134 relative to the anatomy, particularly in areas that are otherwise invisible by fluoroscopy.

Building-out or extension of the model is begun by using system 10 to track catheter 134 in three-dimensions within MPS coordinate system 118. When catheter 134 reaches an end of the reconstructed anatomy, e.g. branch 132, system 10 will use the recorded locations of catheter 134 in order to append portions to the reconstructed model 126. Since the contrast fluid has not reached branches 132 constructed from the recorded locations of catheter 134, only a "centerline" of the added branches will be appended to reconstructed model 126 without lumen contours. The co-registration and motion compensation between the images and models of the various coordinate systems and catheter 134 will help system 10 append the added branches in a way that matches both the actual location of catheter 134 with reconstructed model 126 and the cardiac and respiratory state of the anatomy, e.g., tubular organ 102, with reconstructed model 126, as discussed below.

In another embodiment, catheter 134 collects enhancement data that is used to add a motion component to 3D reconstructed model 126. The motion component is based on the actual motion of the anatomy sensed by a tracked tool, such as catheter 134, while inside of coronary sinus 130. For example, the actual motion data includes local movements of tissue walls within each coordinate system. Thus, even though patient 14 may remain stationary with respect to each coordinate system, tip 136 may move as a heart beats or as lungs respirate and contract. The actual motion data collected can be combined with data used to generate static 3D reconstructed model 126 to add real-time dynamics to 3D reconstructed model 126 simply by manipulating catheter 134 within the region of interest. The motion is synchronized with motion of the anatomy, such as coronary sinus 130, to create a "4D model" that moves in real-time. Thus, 3D reconstructed model 126 may be animated with heart beats, muscular contractions, respiration, etc. In the case of animating 3D reconstructed model 126 with heart beats, the heart beat motions may be gated to a specific time duration of a cardiac cycle, such as the end diastole. The 4D model can be rendered by itself, combined with other images or models, shown on display 16 (FIG. 1), projected on fluoroscopy, etc. For example, a 4D dynamic model of coronary sinus 130 is advantageous for use in a CRT implant procedure where it is desirable to see mechanical heart wall motion patterns.

The co-registration and motion compensation between the images and models of the various coordinate systems and catheter 134 bridges the gap between the real-time motion of catheter 134 and the stable depiction of the anatomy shown by the imaging of static 3D reconstructed model 126. The catheter 134 typically experiences jerky motion while being moved within the anatomy, while the imaging is depicted as a still picture. Using the techniques described herein, a specific location in reconstructed model 126 can be correlated to the current position of catheter 134. A good example would be the placement or parking of catheter 134 at a bifurcation in branches 132. Because of the co-registration and motion compensation, the position of tip 136 on reconstructed model 126 would then be fixed on that bifurcation, regardless of any significant motion that catheter 134 may continuously experience during operation of the device. Now, if catheter 134 is not manipulated or moved, the only components of motion would be the cardiac and respiratory motion of the anatomy. The inherent motion compensation functions of the MediGuide™ system will represent that motion as tip 136 is tracked. Finally, the cardiac and respiratory motion will be applied to the geometry representing that specific bifurcation in 3D reconstructed model 126, hence "mobilizing" or "animating" 3D reconstructed model 126 in a way that is matched to the actual motion of the anatomy, i.e tubular organ 102. Multiple points of the anatomy can be tracked this way to enhance reconstructed model 126 (or parts of it) with motion that represents the actual motion of the anatomy. Any change in the cardiac or respiratory activity of the patient will be reflected automatically in this 4D model. Thus, in aggregate, a system such as the MediGuide™ system keeps track of electrophysiology data, respiration data, patient motions data, etc., and can apply in real-time that data to 3D reconstructed model due to the co-registration and motion compensation capabilities.

The techniques of the present disclosure take advantage of real-time tracking data that is accurately compensated for respiration motion and cardiac motion, and accurately co-registered between different coordinate systems to allow enhancement data collected during active manipulation of the tracked tool to be simultaneously displayed with 3D reconstructed models. The enhancement data shows features not able to be generated in the 3D reconstructed model, which typically comprises a static, historical rendering of the anatomy that may not reflect current conditions of the anatomy. Because of the accuracy of the compensation and registration processes, such as those available with MediGuide™ gMPS™ technology, the enhancement data can be accurately positioned on the 3D reconstructed model in real-time when a physician is most likely to need the information. As such, when a physician is in the middle of a procedure, if the contrast fluid-enhanced X-ray venogram insufficiently shows the area of interest, the procedure can be continued by simply gathering more data with the tracked tool. Furthermore, left ventricular lead placement can be optimized by providing the physician with a visualization of heart wall motion simply by including a tracked tool within the anatomy.

Various embodiments are described herein to various apparatuses, systems, and/or methods. Numerous specific details are set forth to provide a thorough understanding of the overall structure, function, manufacture, and use of the embodiments as described in the specification and illustrated in the accompanying drawings. It will be understood by those skilled in the art, however, that the embodiments may be practiced without such specific details. In other instances, well-known operations, components, and elements have not been described in detail so as not to obscure the embodiments described in the specification. Those of ordinary skill in the art will understand that the embodiments described and illustrated herein are non-limiting examples, and thus it can be appreciated that the specific structural and functional details disclosed herein may be representative and do not necessarily limit the scope of the embodiments.

Although a number of embodiments have been described above with a certain degree of particularity, those skilled in the art could make numerous alterations to the disclosed embodiments without departing from the sprit or scope of this disclosure. For example, all joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the spirit of the disclosure.

Any patent, publication, or other disclosure material, in whole or in part, that is said to be incorporated by referenced herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference.

Reference throughout the specification to "various embodiments," "some embodiments," "one embodiment," or "an embodiment," or the like, means that a particular feature, structure, or characteristic described in connection with the embodiment is included in at least one embodiment. Thus, appearances of the phrases "in various embodiments," "in some embodiments," "in one embodiment," or "in an embodiment," or the like, in places throughout the specification are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features structures, or characteristics of one or more other embodiments without limitation given that such combination is not illogical or non-functional.

What is claimed is:

1. A method for enhancing a three-dimensional (3D) reconstruction of an internal organ of a patient disposed in a tracking space, the method comprising:
   obtaining a signal indicative of a static 3D reconstruction of an object disposed in a 3D tracking space;
   co-registering the 3D reconstruction to the 3D tracking space;
   collecting enhancement data from a tracked elongate medical device disposed in the 3D tracking space; and
   adding real-time features of the object to the static 3D reconstruction using the enhancement data, wherein the static 3D reconstruction is animated in synchronicity with motion of the object based on real-time movement of the tracked elongate medical device engaged with the object to create a 4D model,
   wherein the 3D tracking space is disposed in a Medical Positioning System (MPS) coordinate system and the static 3D reconstruction is disposed in a 3D coordinate system and
   wherein the real-time features comprise an extension of a boundary of the static 3D reconstruction, and wherein the object comprises a heart and the extension of the boundary comprises an extension of a branch of a coronary sinus and
   wherein the object comprises a heart and the extension of the boundary comprises an extension of a branch of a coronary sinus, and
   wherein the branch of the coronary sinus is mapped in the static 3D reconstruction using contrast fluid, and (a) the extension of the boundary extends beyond where the contrast fluid currently terminates, or (b) the contrast fluid is located at the extension of the boundary but has dissipated from an initial concentration effective to visualize the extension.

2. The method of claim 1, wherein the real-time features comprise motion of the object.

3. The method of claim 2, wherein the object comprises a heart and the motion comprises heart wall motion arising from beating of the heart.

4. The method of claim 1, wherein the extension of the boundary of the static 3D reconstruction comprises a trace from the tracked elongate medical device in the MPS coordinate system co-registered with the static 3D reconstruction in the 3D coordinate system.

5. The method of claim 1, wherein the co-registering comprises matching the static 3D reconstruction with an estimated volumetric model generated by the tracked elongate medical device.

6. The method of claim 5, wherein the estimated volumetric model is determined by matching a trace from the tracked elongate medical device with a 2D representation of the object.

7. The method of claim 6, wherein the 2D representation comprises an X-ray image of the object.

8. The method of claim 1, further comprising compensating for movement of the object.

9. The method of claim 8, wherein movement of the object comprises respiration of the patient.

10. The method of claim 9, wherein the compensation comprises synchronizing period frequencies of the 3D reconstruction and the enhancement data.

11. The method of claim 8, wherein movement of the object comprises muscular movement of the internal organ.

12. The method of claim 11, wherein the compensation comprises associating an anchor with the static 3D reconstruction in the 3D coordinate system with the 3D tracking space in the MPS coordinate system.

13. A system for enhancing data acquired from a medical system, the system comprising the following:
a tracked tool in communication with the ECU to provide the second signal; and an electronic control unit (ECU) configured to:
receive a first signal for a static 3D reconstruction of an organ;
co-register the static 3D reconstruction to a 3D tracking space for a tracked elongate medical device;
receive a second signal for enhancement data generated by the tracked elongate medical device operating within a region of interest of the organ; and
add real-time features of the area of interest to the static 3D reconstruction using the enhancement data, wherein the 3D reconstruction is animated in synchronicity with motion of the organ based on real-time movement of the tracked elongate medical device in the organ
wherein the 3D tracking space is disposed in a Medical Positioning System (MPS) coordinate system and the static 3D reconstruction is disposed in a 3D coordinate system and
wherein the real-time features comprise an extension of a boundary of the static 3D reconstruction, and wherein the object comprises a heart and the extension of the boundary comprises an extension of a branch of a coronary sinus and
wherein the object comprises a heart and the extension of the boundary comprises an extension of a branch of a coronary sinus, and
wherein the branch of the coronary sinus is mapped in the static 3D reconstruction using contrast fluid, and (a) the extension of the boundary extends beyond where the contrast fluid currently terminates, or (b) the contrast fluid is located at the extension of the boundary but has dissipated from an initial concentration effective to visualize the extension.

14. The system of claim 13, wherein the extension of the boundary of the static 3D reconstruction comprises a trace from the tracked elongate medical device in a Medical Positioning System (MPS) coordinate system co-registered with the 3D reconstruction in a 3D coordinate system.

15. The system of claim 13, wherein the co-registering comprises matching the static 3D reconstruction with an estimated volumetric model generated by the tracked elongate medical device.

16. The system of claim 15, wherein the estimated volumetric model is determined by matching a trace from the tracked elongate medical device with a 2D representation of the organ.

17. The system of claim 13, wherein the ECU is further configured to compensate for respiration of a patient of the organ.

18. The system of claim 17, wherein the ECU is configured to compensate for respiration of the patient of the organ by synchronizing period frequencies of the 3D reconstruction and the enhancement data.

19. The system of claim 13, wherein the ECU is further configured to compensate for muscular movement of the organ.

20. The system of claim 19, wherein the ECU is further configured to compensate for muscular movement of the organ by associating an anchor with the 3D reconstruction and with the 3D tracking space at a known location.

21. The method of claim 1, wherein the 3D reconstruction includes a centerline data of the branch of the coronary sinus that extends beyond where the contrast fluid currently terminates or (b) the contrast fluid is located at the extension of the boundary but has dissipated from an initial concentration effective to visualize the extension.

22. The method of claim 1, wherein the 4D model is displayed on a display with one or more of an image and a model.

* * * * *